United States Patent [19]

Chu et al.

[11] Patent Number: 4,762,845

[45] Date of Patent: Aug. 9, 1988

[54] 7-(3-SUBSTITUTED IMINO-1-PYRROLIDINYL)-QUINOLONE-3-CARBOXYLIC ACIDS

[75] Inventors: Daniel T. Chu, Vernon Hills; Andre G. Pernet; Curt S. Cooper, both of Lake Bluff, all of Ill.

[73] Assignee: Abbott Laboratories, North Chicago, Ill.

[21] Appl. No.: 866,194

[22] Filed: May 21, 1986

[51] Int. Cl.[4] .................... A61K 31/47; C07D 401/04
[52] U.S. Cl. ..................................... 514/312; 546/156
[58] Field of Search ................. 514/312; 544/363; 546/156

[56] References Cited

U.S. PATENT DOCUMENTS 4,556,658 12/1985 Grohe et al. ..................... 544/128

FOREIGN PATENT DOCUMENTS

| 131839 | 1/1985 | European Pat. Off. |
| 0154780 | 9/1985 | European Pat. Off. ............ 514/314 |
| 3248507 | 7/1984 | Fed. Rep. of Germany ...... 514/312 |

OTHER PUBLICATIONS

Domagala et al., *J. Med. Chem.* 29, pp. 394–404 (3/1986).

*Primary Examiner*—Donald G. Daus
*Assistant Examiner*—Emily Bernhardt
*Attorney, Agent, or Firm*—Steven F. Weinstock; Martin L. Katz

[57] ABSTRACT

New 7-substituted 6-fluoro-1,4-dihydro-4-oxo-quinoline-3-carboxylic acids or esters having a substituted or unsubstituted phenyl radical, an aromatic heterocyclic radical, an alkyl or cycloalkyl radical in the 1-position are antibacterial agents.

6 Claims, No Drawings

7-(3-SUBSTITUTED IMINO-1-PYRROLIDINYL)-QUINOLONE-3-CARBOXYLIC ACIDS

BACKGROUND OF THE INVENTION

This invention relates to new and useful quinoline derivatives having antibacterial properties, to compositions containing the new quinoline derivatives and to methods of treating mammalian patients with the new quinoline derivatives.

It is known that certain 7-piperazinyl-4-oxo-1,4-dihydroquinoline-3-carboxylic acids exhibit antibacterial properties. For example, U.S. Pat. No. 4,017,622 discloses certain 7-piperazinyl-4-oxo-1,4-dihydroquinoline-3-carboxylic aicd derivatives wherein the 1 position substituent is alkyl, benzyl or acetyl. U.S. Pat. No. 4,292,317 discloses certain 7-piperazinyl-6-halo-4-oxo-1,4-dihydroquinoline-3-carboxylic acids are disclosed in which the 1 position substituent may be cycloalkyl, although corresponding derivatives containing a 7-piperazinyl substituent are not disclosed. While the compounds of the foregoing patents may be useful in certain respects, the search continues for new quinoline derivatives which have improved properties or are otherwise useful in the treatment of bacterial infections.

The present invention relates to new 7-substituted 6-fluoro-1,4-dihydro-4-oxo-quinoline-3-carboxylic acids or esters having a substituted or unsubstituted phenyl radical, an aromatic heterocyclic radical, an alkyl or cycloalkyl in the 1 position, to compositions of the new compounds together with pharmaceutically acceptable carriers, and to uses of the new compounds in the treatment of bacterial infections.

DESCRIPTION OF THE PREFERRED EMBODIMENTS

The compounds of the invention can be represented by the following Formula I:

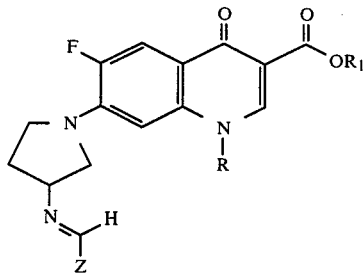

wherein R is lower alkyl, cycloalkyl such as cyclopropyl or is selected from the group consisting of an aromatic heterocyclic ring containing 5 or 6 atoms therein, with the heterocyclic atom being at least one of S, O and N and the remaining atoms being carbon atoms; a phenyl group of the formula:

wherein $R_2$ is one or more hydrogen, halogen, and $C_1$ to $C_4$ alkyl including substituted derivatives thereof said substituted derivatives including haloalkyl, hydroxyalkyl, aminoalkyl and substituted aminoalkyl. $R_1$ is hydrogen or a carboxy-protecting group.

As used herein, the term "aromatic heterocyclic" refers to heterocyclic rings containing 5 or 6 atoms in the ring and containing 1 or 2 heteroatoms selected from the group consisting of S, O or N and the remaining atoms all being carbon atoms. Representative heterocyclic groups include pyridyl, pyrazinyl, thiazolyl, furyl, thienyl and substituted derivatives thereof. Substituents which may be present on the heterocyclic ring include $C_1$ to $C_4$ alkyl groups, halogen groups or a group of the formula $-Y-R_6$ wherein Y is O or S and $R_6$ is hydrogen or $C_1$ to $C_4$ alkyl.

As used herein, the term "halogen" refers to chloro, bromo, fluoro and iodo groups, while the term "$C_1$ to $C_4$ alkyl" refers to lower alkyl groups including methyl, ethyl, propyl, isopropyl, butyl.

As indicated above, $R_2$ can be straight or branched chain $C_1$ to $C_4$ alkyl as well as hydroxy and halo-substituted derivatives thereof. Such groups include a chloromethyl group, a chloroethyl group, a chloropropyl group, a hydroxyethyl group.

As used herein, the term "carboxy-protecting group" refers to and includes the residue of a carboxylic acid ester group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. In general, such carboxy-protecting groups can be relatively easily cleaved to yield the corresponding free carboxy group.

Z is selected from the group consisting of an aromatic heterocyclic ring containing 5 to 6 atoms therein, with the heterocyclic atom being at least one of S, O and N and the remaining atoms being carbon atoms; a phenyl group of the formula:

wherein $R_3$ is one or more of hydrogen, halogen, nitro, carboxyl, cyano, methoxy, methylenedioxy, $C_1$ to $C_4$ alkyl including substituted derivatives thereof, a group having the formula $-Y-R_4$ wherein $-Y-$ is $-O-$ or $-S-$ and $R_4$ is hydrogen or $C_1$ to $C_4$ alkyl, and an amine having the formula:

wherein
$R_5$ and $R_6$ are each independently hydrogen or $C_1$ to $C_4$ alkyl;
Z is also selected from substituted phenyl groups of the formulae A or B

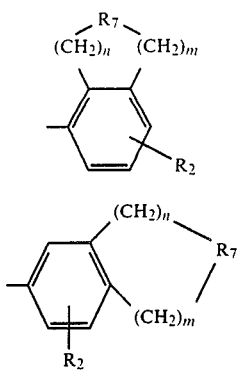

(A)

(B)

wherein n and m can be independently 0, 1, or 2; $R_7$ being selected from S, O, N—$R_8$, or $CH_2$ where $R_8$ is hydrogen, $C_1$ to $C_4$ alkyl, $C_1$ to $C_4$ hydroxyalkyl, $C_1$ to $C_4$ haloalkyl, $C_1$ to $c_4$ aminoalkyl or $C_1$ to $C_4$ alkyl substituted aminoalkyl, as well as the corresponding substituted derivatives thereof and $R_2$ is as described above.

The preferred compounds of the present invention are those having the formula:

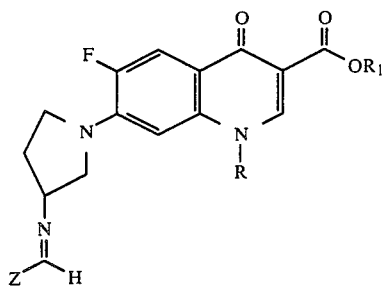

wherein R is $C_1$ to $C_4$ alkyl, or cyclopropyl, a phenyl, or a substituted phenyl wherein the substituent on the phenyl group is one or more of alkyl, halogen, $R_1$ is as described above, and is preferably hydrogen. Z is a phenyl, p-methylphenyl, p-fluorophenyl, 4-pyridine, 2-pyrrole or 2-furan.

Representative of such preferred compounds include 1-p-fluorophenyl-6-fluoro-1,4-dihydro-4-oxo-7-(3-(benzylidene)amino-1-pyrrolidinyl)-quinoline-3-carboxylic acid, 1-p-fluorophenyl-6-fluoro-1,4-dihydro-4-oxo-7-(3-(4-fluorobenzylidene)amino-1-pyrrolidinyl)-quinoline-3-carboxylic acid, 1-p-fluorophenyl-6-fluoro-1,4-dihydro-4-oxo-7-(3-(4-methylbenzylidene)amino-1-pyrrolidinyl)-quinoline-3-carboxylic acid, 1-p-fluorophenyl-6-fluoro-1,4-dihydro-4-oxo-7-(3-(4-pyridylidene)amino-1-pyrrolidinyl)-quinoline-3-carboxylic acid, 1-p-fluorophenyl-6-fluoro-1,4-dihydro-4-oxo-7-(3-(2-pyrrylidene)amino-1-pyrrolidinyl)-quinoline-3-carboxylic acid, 1-p-fluoro-phenyl-6-fluoro-1,4-dihydro-4-oxo-7-(3-(2-furylidene)amino-1-pyrrolidinyl)-quinoline-3-carboxylic acid, 1-o,p-difluorophenyl-6-fluoro-1,4-dihydro-4-oxo-7-(3-(benzylidene)amino-1-pyrrolidinyl)-quinoline-3-carboxylic acid, 1-o,p-difluorophenyl-6-fluoro-1,4-dihydro-4-oxo-7-(3-(p-methylbenzylidene)amino-1-pyrrolidinyl)-quinoline-3-carboxylic acid, 1-o,p-difluorophenyl-6-fluoro-1,4-dihydro-4-oxo-7-(3-(p-fluorobenzylidene)amino-1-pyrrolidinyl)-quinoline-3-carboxylic acid, 1-o,p-difluorophenyl-6-fluoro-1,4-dihydro-4-oxo-7-(3-(4-pyridylidene)amino-1-pyrrolidinyl)-quinoline-3-carboxylic acid, 1-o,p-difluorophenyl-6-fluoro-1,4-dihydro-4-oxo-7-(3-(2-pyrrylidene)amino-1-pyrrolidinyl)-quinoline-3-carboxylic acid, 1-o,p-difluorophenyl-6-fluoro-1,4-dihydro-4-oxo-7-(3-(2-furylidene)amino-1-pyrrolidinyl)-quinoline-3-carboxylic acid, 1-ethyl-6-fluoro-1,4-dihydro-4-oxo-7-(3-(benzylidene)amino-1-pyrrolidinyl)-quinoline-3-carboxylic acid, 1-ethyl-6-fluoro-1,4-dihydro-4-oxo-7-(3-(p-methylbenzylidene)amino-1-pyrrolidinyl)-quinoline-3-carboxylic acid, 1-ethyl-6-fluoro-1,4-dihydro-4-oxo-7-(3-(p-fluorobenzylidene)amino-1-pyrrolidinyl)-quinoline-3-carboxylic acid, 1-ethyl-6-fluoro-1,4-dihydro-4-oxo-7-(3-(4-pyridylidene)amino-1-pyrrolidinyl)-quinoline-3-carboxylic acid, 1-ethyl-6-fluoro-1,4-dihydro-4-oxo-7-(3-(2-pyrrylidene)amino-1-pyrrolidinyl)-quinoline-3-carboxylic acid, 1-ethyl-6-fluoro-1,4-dihydro-4-oxo-7-(3-(2-furylidene)amino-1-pyrrolidinyl)-quinoline-3-carboxylic acid, 1-cyclopropyl-6-fluoro-1,4-dihydro-4-oxo-7-(3-(benzylidene)amino-1-pyrrolidinyl)-quinoline-3-carboxylic acid, 1-cyclopropyl-6-fluoro-1,4-dihydro-4-oxo-7-(3-(p-methylbenzylidene)amino-1-pyrrolidinyl)-quinoline-3-carboxylic acid, 1-cyclopropyl-6-fluoro-1,4-dihydro-4-oxo-7-(3-(p-fluorobenzylidene)amino-1-pyrrolidinyl)-quinoline-3-carboxylic acid, 1-cyclopropyl-6-fluoro-1,4-dihydro-4-oxo-7-(3-(4-pyridylidene)amino-1-pyrrolidinyl)-quinoline-3-carboxylic acid, 1-cyclopropyl-6-fluoro-1,4-dihydro-4-oxo-7-(3-(2-pyrrylidene)amino-1-pyrrolidinyl)-quinoline-3-carboxylic acid, and 1-cyclopropyl-6-fluoro-1,4-dihydro-4-oxo-7-(3-(2-furylidene)amino-1-pyrrolidinyl)-quinoline-3-carboxylic acid.

As used herein, the term "pharmaceutically acceptable salts" means the non-toxic acid addition or alkaline earth metal salts of the compounds of Formula I. These salts can be prepared in situ during the final isolation and purification of the compounds of Formula I, or by separately reacting the base or acid functions with a suitable organic or inorganic acid or base, respectively. Representative acid addition salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, glucoheptonate, lactobionate, lauryl sulfate salts and the like. Representative alkali metal or alkaline earth metal salts include the sodium, calcium, potassium, and magnesium salts, and the like.

It has been found that the preferred compounds of the invention possess antibacterial activity against a wide spectrum of gram positive and gram negative bacteria. The compounds of the invention are therefore useful in the antibiotic treatment of susceptible bacterial infections in both humans and animals. In addition, the compounds may be used in scrub solutions, for surface inhibition of bacterial growth, e.g., on counter surfaces, and the like. Susceptible organisms generally include those gram positive and gram negative, aerobic and anaerobic organisms whose growth can be inhibited by the compounds of the invention, such as Staphylococcus, Lactobacillus, Streptococcus, Sarcina, Escherichia, Enterobacter, Klebsiella, Pseudomonas, Acinetobacter, Proteus, Citrobacter, Nisseria, Baccullus, Bacteroides, Peptococcus, Clostridium, Salmonella, Shigella, Serratia, Haemophilus, Brucella, and other organisms.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administering orally to a mammalian patient suffering from an infection caused by a susceptible organism. If desired, the daily dose may be divided into multiple doses for administration, e.g., two to four times per day.

The compounds of Formula I may be prepared in accordance with the following reaction scheme:

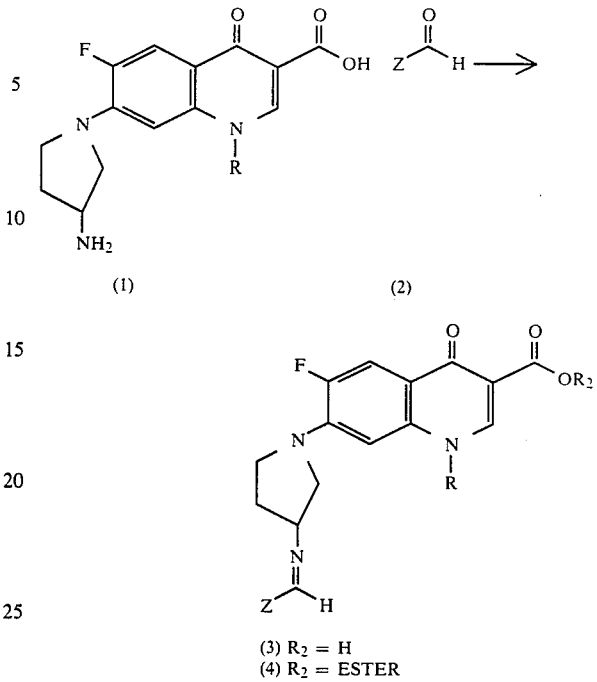

(3) $R_2 = H$
(4) $R_2 = ESTER$

In accordance with the foregoing reaction scheme, the 1-substituted-6-fluoro-1,4-dihydro-4-oxo-7-(3-amino-1-pyrrolidinyl)-quinoline-3-carboxylic acid (1) is reacted with the substituted aldehyde; (2). The formation of the quinoline (3) is conducted in the presence of an aprotic solvent, such as benzene, toluene, xylene, cyclohexane or heptane, and is preferably conducted at temperatures of about 50° to about 145° C., more preferably at the reflux temperature of the solvent employed.

The 1-substituted-6-fluoro-7-substituted-3-amino-1-pyrrolidine-1,4-dihydroxy-4-oxo-quinoline-3-carboxylic acid (3) can then be converted into the corresponding ester (4), if desired, by conventional esterification procedures, such as by treating the free acid (3) with the appropriate alcohol in the presence of an acid catalyst, by converting the free acid (3) into the corresponding acid chloride followed by displacement of the chloro radical with the appropriate alcohol, or by treating the sodium salt of the acid (3) with a suitable reactive halide, such as chloro-methyl pivalate in dimethoxyethane to obtain, for example, the pivaloyloxymethyl ester (4) wherein $R_2$ is $-CH_2OCO(CH_3)_3$.

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the correspondings and substituents in the foregoing scheme.

EXAMPLE 1

1-p-fluorophenyl-6-fluoro-1,4-dihydro-4-oxo-7-(3-(benzylidene)amino-1-pyrrolidinyl)-quinoline-3-carboxylic acid A mixture of 385 mg of 1-p-fluorophenyl-6-fluoro-1,4-dihydro-4-oxo-7-(3-amino-1-pyrrolidinyl)-quinoline-3-carboxylic acid (1) and 255 mg of benzaldehyde in 25 ml of benzene were heated under reflux with stirring under a positive nitrogen atmosphere. Water was removed from the reaction mixture by azeotropic distillation. The reaction mixture was cooled to room temperature and the resulting solid was isolated by suction filtration. The product was washed with benzene (2×10 ml) and was triturated in refluxing methanol. The resulting solid was collected by suction filtration. The filter cake was washed with methanol (2×5 ml) which gave (3), wherein R=p-fluorophenyl and Z=phenyl), m.p. 261°–262° C.

Mass spectrum, M/Z 473.

Analytical Calculation for $C_{27}H_{21}F_2N_3O_3 \cdot \frac{1}{2}H_2O$: C, 67.21; H, 4.60; N, 8.71. Found: C, 67.23; H, 4.49; N, 8.67.

EXAMPLE 2

1-p-fluorophenyl-6-fluoro-1,4-dihydro-4-oxo-7-(3-(4-fluorobenzylidene)amino-1-pyrrolidinyl)-quinoline-3-carboxylic acid The procedure of Example 1 is repeated replacing benzaldehyde with 4-fluorobenzaldehyde to obtain 1-p-fluorophenyl-6-fluoro-1,4-dihydro-4-oxo-7-(3-(4-fluorobenzylidene)amino-1-pyrrolidinyl)-quinoline-3-carboxylic acid (3) (R=p-fluorophenyl, Z=p-fluorophenyl).

mp 242°–243° C.

Mass Spectrum, M/Z 491.

Analytical Calculation for $C_{27}H_{20}F_3N_3O_3$: C, 65.98; H, 4.10; N, 8.55. Found: C, 65.77; H, 4.11; N, 8.51.

EXAMPLE 3

1-p-fluorophenyl-6-fluoro-1,4-dihydro-4-oxo-7-(3-(4-methylbenzylidene)amino-1-pyrrolidinyl)-quinoline-3-carboxylic acid The procedure of example 1 is repeated replacing benzaldehyde with 4-methylbenzaldehyde to obtain 1-p-fluorophenyl-6-fluoro-1,4-dihydro-4-oxo-7-(3-(4-methylbenzylidene)amino-1-pyrrolidinyl)-quinoline-3-carboxylic acid (3) (R=p-fluorophenyl, Z=p-methylphenyl.

mp 257°–258° C. Mass Spectrum, M/Z 487.

Analytical Calculation for $C_{28}H_{23}F_2N_3O_3$: C, 68.99; H, 4.72; N, 8.62. Found: C, 69.11; H, 4.79; N, 8.54.

EXAMPLE 4

1-p-fluorophenyl-6-fluoro-1,4-dihydro-4-oxo-7-(3-(4-pyridylidene)amino-1-pyrrolidinyl)-quinoline-3-carboxylic acid The procedure of Example 1 is repeated replacing benzaldehyde with 4-pyridinecarboxaldehyde to obtain 1-p-fluorophenyl-1,4-dihydro-4-oxo-7-(3-(4-pyridylidene)amino-1-pyrrolidinyl)-quinoline-3-carboxylic acid (3) (R=p-fluorophenyl, Z=4-pyridine).

mp 274°–265° C. (Decomp).

Mass Spectrum, M/Z 474.

Analytical Calculation for $C_{26}H_{20}OF_2N_4O_3$: C, 65.81; H, 4.25; N, 11.81. Found: C, 65.26; H, 4.17; N, 11.49.

EXAMPLE 5

1-p-fluorophenyl-6-fluoro-1,4-dihydro-4-oxo-7-(3-(2-pyrrylidene)amino-1-pyrrolidinyl)-quinoline-3-carboxylic acid The procedure of Example 1 is repeated replacing benzaldehyde with 2-pyrrolecarboxaldehyde to obtain 1-p-fluorophenyl-6-fluoro-1,4-dihydro-4-oxo-7-(3-(2-pyrrylidene)amino-1-pyrrolidinyl)-quinoline-3-carboxylic acid (3) (R=p-fluorophenyl, Z=2-pyrrole).

mp 276°–277° C. (Decomp).

Mass Spectrum, M/Z 462.

Analytical Calculation for $C_{25}H_{20}F_2N_4O_3 \cdot \frac{1}{4}H_2O$: C, 64.30; H, 4.42; N, 12.00. Found: C, 64.24; H, 4.33; N, 11.62.

EXAMPLE 6

1-p-fluorophenyl-6-fluoro-1,4-dihydro-4-oxo-7-(3-(2-furylidene)amino-1-pyrrolidinyl)-quinoline-3-carboxylic acid The procedure of Example 1 is repeated replacing benzaldehyde with 2-furaldehyde to obtain 1-p-fluorophenyl-6-fluoro-1,4-dihydro-4-oxo-7-(3-(2-furylidene)amino-1-pyrrolidinyl)-quinoline-3-carboxylic acid (3) (R=fluorophenyl, Z=2-furan).

mp 257°–258° C.

Mass Spectrum, M/Z 463.

Analytical Calculation for $C_{25}H_{19}F_2N_3O_4$: C, 64.79; H, 4.13; N, 9.07. Found: C, 64.58; H, 4.22; N, 8.87.

EXAMPLE 7

1-o,p-difluorophenyl-6-fluoro-1,4-dihydro-4-oxo-7-(3-(benzylidene)amino-1-pyrrolidinyl)-quinoline-3-carboxylic acid The procedure of Example 1 is repeated replacing 1-p-fluorophenyl-6-fluoro-1,4-dihydro-4-oxo-7-(3-amino-1-pyrrolidinyl)-quinoline-3-carboxylic acid with 1-o,p-difluorophenyl-6-fluoro-1,4-dihydro-4-oxo-7-(3-amino-1-pyrrolidinyl)-quinoline-3-carboxylic acid (1) to obtain 1-o,p-difluorophenyl-6-fluoro-1,4-dihydro-4-oxo-7-(3-(benzylidene)amino-1-pyrrolidinyl)-quinoline-3-carboxylic acid (3) (R=o,p-difluorophenyl, Z=phenyl).

EXAMPLE 8

1-o,p-difluorophenyl-6-fluoro-1,4-dihydro-4-oxo-7-(3-(p-methylbenzylidene)amino-1-pyrrolidinyl)-quinoline-3-carboxylic acid In the described fashion of Example 1 replacing benzaldehyde with p-methylbenzaldehyde and using the acid (1) (R=o,p-difluorophenyl) described in Example 7 one obtains 1-o,p-difluorophenyl-6-fluoro-1,4-dihydro-4-oxo-7-(3-(p-methylbenzylidene)amino-1-pyrrolidinyl)-quinoline-3-carboxylic acid (3) (R=o,p-difluorophenyl, Z=p-methylphenyl).

EXAMPLE 9

1-o,p-difluorophenyl-6-fluoro-1,4-dihydro-4-oxo-7-(3-(p-fluorobenzylidene)amino-1-pyrrolidinyl)-quinoline-3-carboxylic acid In the described fashion of Example 1 replacing benzaldehyde with p-fluorobenzaldehyde and using the acid (1) (R=o,p-difluorophenyl) described in Example 7, one obtains 1-o,p-difluorophenyl-6-fluoro-1,4-dihydro-4-oxo-7-(3(p-fluorobenzylidene)amino-1-pyrrolidinyl)-quinoline-3-carboxylic acid (3) (R=o,p-difluorophenyl, Z=p-fluorophenyl).

EXAMPLE 10

1-o,p-difluorophenyl-6-fluoro-1,4-dihydro-4-oxo-7-(3-(4-pyridylidene)amino-1-pyrrolidinyl)-quinoline-3-carboxylic acid In the described fashion of Example 1 replacing benzaldehyde with 4-pyridinecarboxaldehyde and using the acid (1) R=o,p-difluorophenyl) described in Example 7 one obtains 1-o,p-difluorophenyl-6-fluoro-1,4-dihydro-4-oxo-7-(3-(4-pyridylidene)amino-1-pyrrolidinyl)quinoline-3-carboxylic acid (3) (R=o,p-difluorophenyl, Z=4-pyridine).

EXAMPLE 11

1-o,p-difluorophenyl-6-fluoro-1,4-dihydro-4-oxo-7-(3-(2-pyrrylidene)amino-1-pyrolidinyl)-quinoline-3-carboxylic acid In the described fashion of Example 1 replacing benzaldehyde with 2-pyrrolecarboxyaldehyde and using the acid (1) (R=o,p-difluorophenyl) described in Example 7 one obtains 1-o,p-difluoro-4-oxo-7-(3-(2-pyrrylidene)amino-1-pyrrolidinyl)-quinoline-3-carboxylic acid (3) (R=o,p-difluorophenyl, Z=2-pyrrole).

EXAMPLE 12

1-o,p-difluorophenyl-6-fluoro-1,4-dihydro-4-oxo-7-(3-(2-furylidene)amino-1-pyrrolidinyl)-quinoline-3-carboxylic acid In the described fashion of Example 1 replacing benzaldehyde with 2-furaldehyde and using the acid (1) (R=o,p-difluorophenyl) described in Example 7 one can obtain 1-o,p-difluorophenyl-6-fluoro-1,4-dihydro-4-oxo-7-(3-(2-furylidene)amino-1-pyrrolidinyl)-quinoline-3-carboxylic acid (3) (R=o,p-difluorophenyl, Z=2-furan).

EXAMPLE 13

1-ethyl-6-fluoro-1,4-dihydro-4-oxo-7-(3-(benzylidene)amino-1-pyrrolidinyl)-quinoline-3-carboxylic acid The procedure of Example 1 can be repeated replacing 1-p-fluorophenyl-6-fluoro-1,4-dihydro-4-oxo-7-(3-amino-1-pyrrolidinyl)-quinoline-3-carboxylic acid(1) (R=p-fluorophenyl) with 1-ethyl-6-fluoro-1,4-dihydro-4-oxo-7-(3-amino-1-pyrrolidinyl)quinoline-3-carboxylic acid (1) (R=ethyl) to obtain 1-ethyl-6-fluoro-1,4-dihydro-4-oxo-7-(3-(benzylidene) amino-1-pyrrolidinyl)-quinoline-3-carboxylic acid (3) (R=ethyl, Z=phenyl).

EXAMPLE 14

1-ethyl-6-fluoro-1,4-dihydro-4-oxo-7-(3-(p-methylbenzylidene)amino-1-pyrrolidinyl)-quinoline-3-carboxylic acid In the described fashion of Example 1 replacing benzaldehyde with p-methylbenzaldehyde and using the acid (1) (R=ethyl) described in example 13 one obtains 1-ethyl-6-fluoro-1,4-dihydro-4-oxo-7-(3-p-methylbenzylidene)amino-1-pyrrolidinyl)-quinoline-3-carboxylic acid (3) (R=ethyl-Z=p-methylphenyl).

EXAMPLE 15

1-ethyl-6-fluoro-1,4-dihydro-4-oxo-7-(3-(p-fluorobenzylidene)amino-1-pyrrolidinyl)-quinoline-3-carboxylic acid In the described fashion of Example 1 replacing benzaldehyde with p-fluorobenzyldehyde and using the acid (1) (R=ethyl) described in Example 13 one obtains 1-ethyl-6-fluoro-1,4-dihydro-4-oxo-7-(3-(p-fluorobenzylidene)amino-1-pyrrolidinyl)-quinoline-3-carboxylic acid (3) (R=ethyl, Z=p-fluorophenyl).

EXAMPLE 16

1-ethyl-6-fluoro-1,4-dihydro-4-oxo-7-(3-(4-pyridylidene)amino-1-pyrrolidinyl)-quinoline-3-carboxylic acid In the described fashion of Example 1 replacing benzaldehyde with 4-pyridinecarboxaldehyde and using the acid (1) (R=ethyl) described in Example 13 one obtains 1-ethyl-6-fluoro-1,4-dihydro-4-oxo-7-(3-(4-pyridylidene)amino-1-pyrrolidinyl)-quinoline-3-carboxylic acid (3) (R=ethyl, Z=4-pyridine).

EXAMPLE 17

1-ethyl-6-fluoro-1,4-dihydro-4-oxo-7-(3-(2-pyrrylidene)amino-1-pyrrolidinyl)-quinoline-3-carboxylic acid In the described fashion of Example 1 replacing benzaldehyde with 2-pyrrolecarboxyalde and using the acid (1) (R=ethyl) described in Example 13 one can obtain 1-ethyl-6-fluoro-1,4-dihydro-4-oxo-7-(3-(2-pyrrylidene)amino-1-pyrrolidinyl)-quinoline-3-carboxylic acid (3) (R=ethyl, Z=2-pyrrole).

EXAMPLE 18

1-ethyl-6-fluoro-1,4-dihydro-4-oxo-7-(3-(2-furylidene)amino-1-pyrrolidinyl)-quinoline-3-carboxylic acid In the described fashion of Example 1 replacing benzaldehyde with 2-furaldehyde and using the acid (1) (R=ethyl) described in Example 13 one obtains 1-ethyl-6-fluoro-1,4-dihydro-4-oxo-7-(3-(2-furylidene)amino-1-pyrrolidinyl)-quinoline-3-carboxylic acid (3) (R=ethyl, Z=2-furan).

EXAMPLE 19

1-cyclopropyl-6-fluoro-1,4-dihydro-4-oxo-7-(3-benzylidene)amino-1-pyrrolidinyl)-quinoline-3-carboxylic acid The procedure of Example 1 is repeated replacing 1-p-fluorophenyl-6-fluoro-1,4-dihydro-4-oxo-7-(3-amino-1-pyrrolidinyl)-quinoline-3-carboxylic acid (1) (R=p-fluorophenhyl) with 1-cyclopropyl-6-fluoro-1,4-dihydro-4-oxo-7-(3-amino-1-pyrrolidinyl)quinoline-3-carboxylic acid (1) (R=cyclopropyl) to obtain 1-cyclopropyl-6-fluoro-1,4-dihydro-4-oxo-7-(3-(benzylidene)amino-1-pyrrolidinyl)-quinoline-3-carboxylic acid (3) (R-=cyclopropyl, Z=phenyl).

EXAMPLE 20

1-cyclopropyl-6-fluoro-1,4-dihydro-4-oxo-7-(3-(p-methylbenzylidene)amino-1-pyrrolidinyl)-quinoline-3-carboxylic acid In the described fashion of Example 1 replacing benzaldehyde with p-methylbenzaldehyde and using the acid (1) (R=cyclopropyl) described in Example 19 one obtains 1-cyclopropyl-6-fluoro-1,4-dihydro-4-oxo-7-(3-(p-methylbenzylidene)amino-1-pyrrolidinyl)-quinoline-3-carboxylic acid (3) (R=cyclopropyl, Z=p-methylphenyl).

EXAMPLE 21

1-cyclopropyl-6-fluoro-1,4-dihydro-4-oxo-7-(3-(p-fluorobenzylidene)amino-1-pyrrolidinyl)-quinoline-3-carboxylic acid In the described fashion of Example 1 replacing benzaldehyde and p-fluorobenzaldehyde and using the acid (1) (R=cyclopropyl) described in Example 19 one obtains 1 cyclopropyl-6-fluoro-1,4-dihydro-4-oxo-7-(3-(p-fluorobenzylidene)amino-1-pyrrolidinyl)-quinoline-3-carboxylic acid (3) (R=cyclopropyl, Z=p-fluorophenyl). mp 228°–229° C.

Mass Spectrum, M/Z 437.

Analytical Calculation for $C_{24}H_{21}F_2N_3O_3.H_2O$: C, 63.28; H, 5.09; N, 9.23. Found: C, 63.50; H, 5.13; N, 9.52.

EXAMPLE 22

1-cyclopropyl-6-fluoro-1,4-dihydro-4-oxo-7-(3-(4-pyridylidene)amino-1-pyrrolidinyl)-quinoline-3-carboxylic acid In the described fashion of Example 1 replacing benzaldehyde with 4-pyridinecarboxaldehyde and using the acid (1) (R=cyclopropyl) described in example 19 one obtains 1-cyclopropyl-6-fluoro-1,4-dihydro-4-oxo-7-(3-(4-pyridylidene)amino-1-pyrrolidinyl)-quinoline-3-carboxylic acid (3); (R=cyclopropyl, Z=4-pyridine). mp 233°–234° C.

Mass Spectrum, M/Z 420.

Analytical Calculation for $C_{23}H_{21}FN_4O_3.H_2O$: C, 63.01; H, 5.29; N, 12.78. Found: C, 63.51; H, 5.23; N, 12.69.

EXAMPLE 23

1-cyclopropyl-6-fluoro-1,4-dihydro-4-oxo-7-(3-(2-pyrrolidene)amino-1-pyrrolidinyl)-quinoline-3-carboxylic acid In the described fashion of Example 1 replacing benzaldehyde with with 2-pyrrolecarboxaldehyde and using the acid (1) (R=cyclopropyl) described in Example 19 one can obtain 1-cyclopropyl-6-fluoro-1,4-dihydro-4-oxo-7-(3-(2-pyrrylidene)amino-1-pyrrolidinyl)-quinoline-3-carboxylic acid (3) (R=cyclopropyl, Z=2-pyrrole).

EXAMPLE 24

1-cyclopropyl-6-fluoro-1,4-dihydro-4-oxo-7-(3-(2-furylidene)amino-1-pyrrolidinyl)-quinoline-3-carboxylic acid In the described fashion of Example 1 replacing benzaldehyde with 2-furaldehyde and using the acid (1) (R=cyclopropyl) described in Example 19 one obtains 1-cyclopropyl-6-fluoro-1,4-dihydro-4-oxo-7-(3-(2-furylidene)amino-1-pyrrolidinyl)-quinoline-3-carboxylic acid (3) (R=cyclopropyl, Z=2-furan).

EXAMPLE 25

1-p-fluorophenyl-6-fluoro-1,4-dihydro-4-oxo-7-(3-(cyclopentylidene)amino-1-pyrrolidinyl)-quinoline-3-carboxylic acid The procedure of Example 1 can be repeated replacing benzaldehyde with cyclopentanone to obtain 1-p-fluorophenyl-6-fluoro-1,4-dihydro-4-oxo-7-(3-(cyclopentylidene)amino-1-pyrrolidinyl)-quinoline-3-carboxylic acid (3) (R=p-fluorophenyl, Z=cyclopentanyl).

EXAMPLE 26

1-p-fluorophenyl-6-fluoro-1,4-dihydro-4-oxo-7-(3-(4-nitrobenzylidene)amino-1-pyrrolidinyl)-quinoline-3-carboxylic acid The procedure of Example 1 is repeated replacing benzaldehyde with 4-nitrobenzaldehyde to obtain 1-p-fluorophenyl-6-fluoro-1,4-dihydro-4-oxo-7-(3-(4-nitrobenzylidene)amino-1-pyrrolidinyl)quinoline-3-carboxylic acid (3) (R=p-fluorophenyl, Z=p-nitrophenyl), m.p. 242°–243° C.; Mass Spectrum, M/Z 518; Analytical Calculation for $C_{27}H_{20}F_2N_4O_5.\frac{1}{2}H_2$): C, 61.47; H 4.01; N, 10.62. Found: 61.49; H, 3.87; N, 10.36.

EXAMPLE 27

1-p-fluorophenyl-6-fluoro-1,4-dihydro-4-oxo-7-(3-(3-pyridylidene)amino-1-pyrrolidinyl)-quinoline-3-carboxylic acid The procedure of Example 1 is repeated replacing benzaldehyde with 3-pyridinecarboxaldehyde to obtain 1-p-fluorophenyl-6-fluoro-1,4-dihydro-4-oxo-7-(3-(3-pyridylidene)amino-1-pyrrolidinyl)-quinoline-3-carboxylic acid (3) (R=p-fluorophenyl, Z=3-pyridine), m.p. 247°–248° C. (Decomp): Mass Spectrum, M/Z 474; Analytical Calculation for $C_{26}H_{20}F_2N_4O_3$: C, 65.81; H, 4.25; N, 11.81. Found: C, 65.66; H, 4.20; N, 11.65.

EXAMPLE 28

1-p-fluorophenyl-6-fluoro-1,4-dihydro-4-oxo-7-(3-(2-pyridylidene)amino-1-pyrrolidinyl)-quinoline-3-carboxylic acid The procedure of Example 1 is repeated replacing benzaldehyde with 2-pyridenecarboxaldehyde to obtain 1-p-fluorophenyl-6-fluoro-1,4-dihydro-4-oxo-7-(3-(2-pyridylidene)amino-1-pyrrolidinyl)-quinoline-3-carboxylic acid (3) (R=p-fluorophenyl, Z=2-pyridine); m.p. 261°–262° C. (Decomp); Mass Spectrum, M/Z 474; Analytical Calculation for $C_{26}H_{20}F_2N_4O_3$: C, 65.81; H, 4.25; N, 11.81. Found: C, 65.93; H, 4.23; N, 11.72.

EXAMPLE 29

1-p-fluorophenyl-6-fluoro-1,4-dihydro-4-oxo-7-(3-(4-methoxybenzylidene)amino-1-pyrrolidinyl)-quinoline-3-carboxylic acid The procedure of Example 1 is repeated replacing benzaldehyde with 4-methoxybenzaldehyde to obtain 1-p-fluorophenyl-6-fluoro-1,4-dihydro-4-oxo-7-(3-(4-methoxybenzylidene)amino-1-pyrrolidinyl)-quinoline-3-carboxylic acid (3) (R=p-fluorophenyl, Z=p-methoxyphenyl); m.p. 266°–267° C.; Mass Spectrum, M/Z 504; Analytical Calculation for $C_{28}H_{23}F_2N_3O_4$: C, 66.80; H, 4.57; N, 8.35. Found: C, 66.62; H, 4.58; N, 8.23.

EXAMPLE 30

1-p-fluorophenyl-6-fluoro-1,4-dihydro-4-oxo-7-(3-(2-hydroxybenzylidene)amino-1-pyrrolidinyl)-quinoline-3-carboxylic acid The procedure of Example 1 is repeated replacing benzaldehyde with 2-hydroxybenzaldehyde to obtain 1-p-fluorophenyl-6-fluoro-1,4-dihydro-4-oxo-7-(3-(2-hydroxybenzylidene)amino-1-pyrrolidinyl)-qunoline-3-carboxylic acid (3) R=p-fluorophenyl, Z=o-hydroxyphenyl); m.p.>300° C.; Mass Sepctrum, M/Z 489; Analytical Calculation for $C_{27}H_{21}F_2N_3O_4$: C, 66.26; H, 4.29; N, 8.59. Found: C, 66. 23; H, 4.33; N, 8.54.

EXAMPLE 31

1-p-fluorophenyl-6-fluoro-1,4-dihydro-4-oxo-7-(3-(4-cyanobenzylidene)amino-1-pyrrolidinyl)-quinoline-3-carboxylic acid The procedure of Example 1 is repeated replacing benzaldehyde with 4-cyanobenzaldehyde to obtain 1-p-fluorophenyl-6-fluoro-1,4-dihydro-4-oxo-7-(3-(4-cyanobenzylidene)amino-1-pyrrolidinyl)-quinoline-3-carboxylic acid (3) (R=p-fluorophenyl, Z=p-cyanophenyl); m.p. 270°–271° C.; Mass Spectrum, M/Z 498; Analytical Calculation for $C_{28}H_2OF_2N_4O_3.\frac{1}{2}H_2O$: C, 67.47; H, 4.02, N, 11.24. Found: C, 66.64; H, 4.02; N, 10.90.

EXAMPLE 32

1-p-fluorophenyl-6-fluoro-1,4-dihydro-4-oxo-7-(3-(2-methylbenzylidene)amino-1-pyrrolidinyl)-quinoline-3-carboxylic acid The procedure of Example 1 is repeated replacing benzaldehyde with 2-methylbenzaldehyde to obtain 1-p-fluorophenyl-6-fluoro-1,4-dihydro-4-oxo-7-(3-(2-methylbenzylidene)amino-1-pyrrolidinyl)-quinoline-3-carboxylic acid (3) (R=p-fluorophenyl, Z=o-methylphenyl); m.p. 285°–286° C.; Mass Spectrum, M/Z 487; Analytical Calculation for $C_{28}H_{23}F_2N_3O_3$: C, 68.99; H, 4.72; N, 8.62. Found: C, 68.94; H, 4.81; N, 8.53.

EXAMPLE 33

1-cyclopropyl-6-fluoro-1,4-dihydro-4-oxo-7-(3-(4-hydroxybenzylidene)amino-1-pyrrolidinyl)-quinoline-3-carboxylic acid In the described fashion of Example 1 replacing benzaldehyde with 4-hydroxybenzaldehyde and using the acid (1) (R=cyclopropyl) described in Example 19 one obtains 1-cyclopropyl-6-fluoro-1,4-dihydro-4-oxo-7-(3-(4-hydroxybenzylidene)amino-1-pyrrolidinyl)-quinoline-3-carboxylic acid (3) (R=cyclopropyl, Z=p-hydroxyphenyl); m.p. 273°–275° C.; Mass Spectrum, M/Z 435. Analytical Calculation for $C_{24}H_{22}FN_3O_4.\frac{1}{2}H_2O$: C, 66.21; H, 5.06; N, 9.65. Found: C, 64.83; H, 5.01; N, 9.13.

EXAMPLE 34

1-cyclopropyl-6-fluoro-1,4-dihydro-4-oxo-7-(3-(4-aminobenzylidene)amino-1-pyrrolidinyl)-quinoline-3-carboxylic acid In the described fashion of Example 1 replacing benzaldehyde with 4-aminobenzaldehyde and using the acid (1) (R=cyclopropyl) described in Example 19 one obtains 1-cyclopropyl-6-fluoro-1,4-dihydro-4-oxo-7-(3-(4-aminobenzylidene)amino-1-pyrrolidinyl)-quinoline-3-carboxylic acid (3) (R=cyclopropyl, Z=p-aminophenyl).

EXAMPLE 35

1-p-fluorophenyl-6-fluoro-1,4-dihydro-4-oxo-7-(3-(4-carboxybenzylidene)amino-1-pyrrolidinyl)-quinoline-3-carboxylic acid In the described fashion of example 1 replacing benzaldehyde with 4-carboxybenzaldehyde one obtains 1-p-fluorophenyl-6-fluoro-1,4-dihydro-4-oxo-7-(3-(4-carboxybenzylidene)amino-1-pyrrolidinyl)-quinoline-3-carboxylic acid(3) (R=fluorophenyl, Z=4-carboxyphenyl).

EXAMPLE 36

1-cyclopropyl-6-fluoro-1,4-dihydro-4-oxo-7-(3-(4-N,N-dimethylaminobenzylidene)amino-1-pyrrolidinyl)-quinoline-3-carboxylic acid In the described fashion of Example 1 replacing benzaldehyde with 4-N,N-dimethylaminobenzaldehyde and using the acid (1) (R=cyclopropyl) described in Example 19 one obtains 1-cyclopropyl-6-fluoro-1,4-dihydro-4-oxo-7-(3-(4-N,N-dimethylaminobenzylidene)amino-1-pyrrolidinyl)-quinoline-3-carboxylic acid (3) (R=cyclopropyl, Z=4-N,N-dimethylaminophenyl).

EXAMPLE 37

1-ethyl-6-fluoro-1,4-dihydro-4-oxo-7-(3-(4-N,N-dimethylaminomethylbenzylidene)amino-1-pyrrolidinyl)-quinoline-3-carboxylic acid In the described fashion of Example 1 replacing benzaldehyde with 4-N,N-dimethylaminomethylbenzaldehyde and using the acid (1) (R=ethyl) described in Example 13 one obtains 1-ethyl-6-fluoro-1,4-dihydro-4-oxo-7-(3-(4-N,N-dimethylaminomethylbenzylidene)amino-1-pyrrolidinyl)-quinoline-3-carboxylic acid (3) (R=ethyl, Z=4-N,N-dimethylaminomethylphenyl).

EXAMPLE 38

1-p-fluorophenyl-6-fluoro-1,4-dihydro-4-oxo-7-(3-(4-N-(2-chloroethyl)aminomethylbenzylidene)amino-1-pyrroli-dinyl)-quinoline-3-carboxylic acid In the described fashion of Example 1 replacing benzaldehyde with 4-N-(2-chloroethyl)aminomethylbenzaldehyde one obtains 1-p-fluorophenyl-6-fluoro-1,4-dihydro-4-oxo-7-(3-(4-N-(2-chloroethyl)aminomethylbenzylidene)amino-1-pyrrolidinyl)-quinoline-3-carboxylic acid (3) (R=p-fluorophenyl, Z=4-N-(2-chloroethyl)aminomethylphenyl).

EXAMPLE 39

1-p-fluorophenyl-6-fluoro-1,4-dihydro-4-oxo-7-(3-(4-N-(2-hydroxyethyl)aminomethylbenzylidene)amino-1-pyrrol-idinyl)-quinoline-3-carboxylic acid In the described fashion of Example 1 replacing benzaldehyde with 4-N-(2-hydroxyethyl)aminomethylbenzaldehyde one obtains fluorophenyl-6-fluoro-1,4-dihydro-4-oxo-7-(3-(4-N-(2-hydroxyethyl)aminomethylbenzylidene)amino-1-pyrrolidinyl)-quinioline-3-carboxylic acid (3) (R=p-fluorophenyl, Z=4-N-(2-hydroxyethyl)aminomethylphenyl).

EXAMPLE 40

1-cyclopropyl-6-fluoro-1,4-dihydro-4-oxo-7-(3-(4-N(2-aminoethyl)aminomethylbenzylidene)amino-1-pyrrolidinyl)-quinoline-3-carboxylic acid In the described fashion of Example 1 replacing benzaldehyde with 4-N-(2-aminoethyl)aminoethylbenzaldehyde and using the acid (1) (R=cyclopropyl) described in Example 19 one obtains 1-cyclopropyl-6-fluoro-1,4-dihydro-4-oxo-7-(3-(4-N-(2-aminoethyl)aminomethylbenzylidene)amino-1-pyrrolidinyl)-quinoline 3-carboxylic acid (3) (R=cyclopropyl, Z=4-N-(2-aminoethyl)aminomethylphenyl).

EXAMPLE 41

In similar fashion as Example 1, the use of various 1-substituted-7-(3-amino-1-pyrrolidinyl)-1,4-dihydro-4- oxo-quinoline-3-carboxylic acids (1), wherein R is ethyl, cyclopropyl, p-fluorophenyl or o,p-difluorophenyl and benzaldehyde is replaced with appropriate substituted benzaldehydes the following additional compounds (3) are made as summarized in Table I.

TABLE I

| Benzaldehyde Replacement | Acid (1) R | Compound (3) Z | Obtained R |
|---|---|---|---|
| 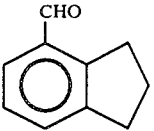 | cyclopropyl | 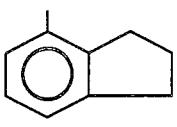 | cyclopropyl |
| 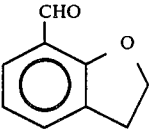 | ethyl | 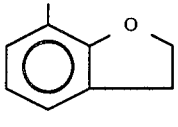 | ethyl |
| 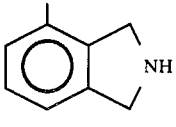 | p-fluorophenyl | 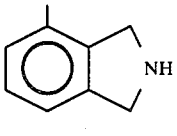 | p-fluorophenyl |
| 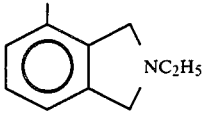 | o,p-difluorophenyl | 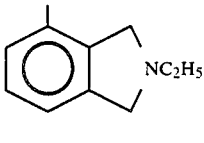 | o,p-difluorophenyl |
| 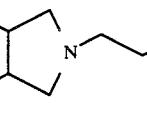 | cyclopropyl | 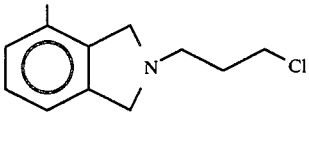 | cyclopropyl |
| 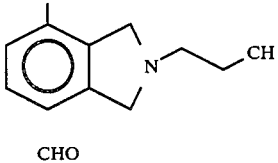 | ethyl | 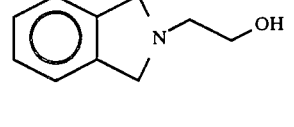 | ethyl |
| 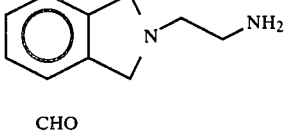 | p-fluorophenyl | 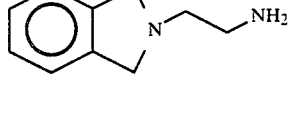 | p-fluorophenyl |
| 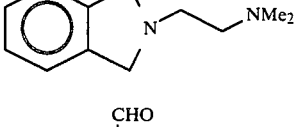 | o-p-difluorophenyl | 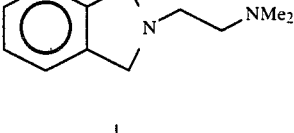 | o,p-difluorophenyl |
| 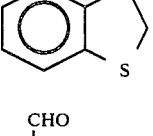 | cyclopropyl | 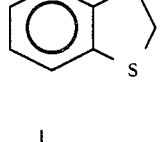 | cyclopropyl |
| 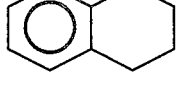 | ethyl | 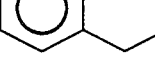 | ethyl |

TABLE I-continued

| Benzaldehyde Replacement | Acid (1) R | Compound (3) Z | Obtained R |
|---|---|---|---|
| 2-CHO isochroman | p-fluorophenyl | 5-methyl isochroman | p-fluorophenyl |
| 2-CHO isothiochroman | o,p-difluorophenyl | 5-methyl isothiochroman | o,p-difluorophenyl |
| 2-CHO 1,2,3,4-tetrahydroquinoline | cyclopropyl | 5-methyl 1,2,3,4-tetrahydroquinoline | cyclopropyl |
| 2-CHO 2-(2-aminoethyl)-1,2,3,4-tetrahydroisoquinoline | ethyl | 5-methyl 2-(2-aminoethyl)-1,2,3,4-tetrahydroisoquinoline | ethyl |
| CHO 2-(3-dimethylaminopropyl)-1,2,3,4-tetrahydroisoquinoline | p-fluorophenyl | methyl 2-(3-dimethylaminopropyl)-1,2,3,4-tetrahydroisoquinoline | p-fluorophenyl |
| 5-CHO indane | o,p-difluorophenyl | 5-methyl indane | o,p-difluorophenyl |
| 5-CHO 1,3-dihydroisobenzofuran | cyclopropyl | 5-methyl 1,3-dihydroisobenzofuran | cyclopropyl |
| 5-CHO 2,3-dihydrobenzothiophene | ethyl | 5-methyl 2,3-dihydrobenzothiophene | ethyl |
| 5-CHO indoline | p-fluorophenyl | 5-methyl indoline | p-fluorophenyl |

TABLE I-continued

| Benzaldehyde Replacement | Acid (1) R | Compound (3) Z | Obtained R |
|---|---|---|---|
| 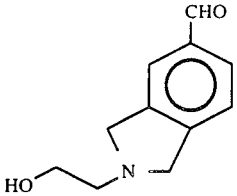 | o,p-difluorophenyl | 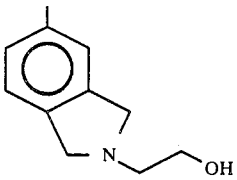 | o,p-difluorophenyl |
| 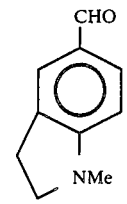 | cyclopropyl | 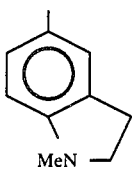 | cyclopropyl |
| 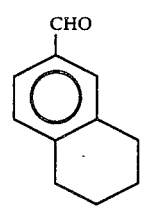 | ethyl | 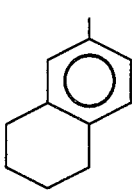 | ethyl |
| 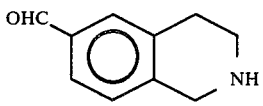 | p-fluorophenyl | 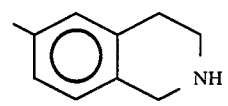 | p-fluorophenyl |
| 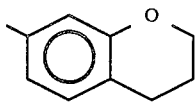 | o,p-difluorophenyl | 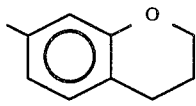 | o,p-difluorophenyl |
| 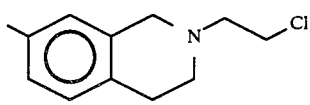 | cyclopropyl | 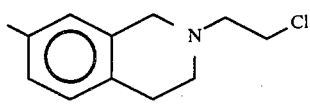 | cyclopropyl |
| 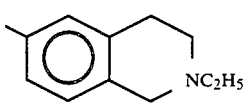 | ethyl | 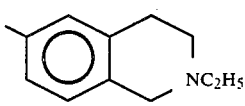 | ethyl |
| 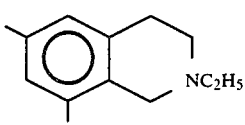 | cyclopropyl | 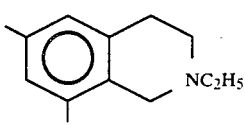 | cyclopropyl |
| 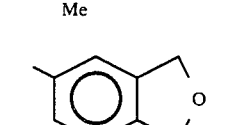 | ethyl | 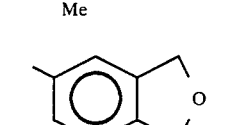 | ethyl |
| 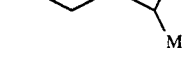 | p-fluorophenyl | 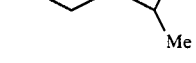 | p-fluorophenyl |

It will be understood that various changes and modifications can be made in the details of procedure, formu-

We claim:
1. A compound of the Formula I:

[Structure: 6-fluoro-7-(3-(formylimino)pyrrolidin-1-yl)-4-oxo-1-R-1,4-dihydroquinoline-3-carboxylate, with OR₁ ester, N-R on quinoline nitrogen, and pyrrolidine substituent bearing N=CH-Z group]

wherein R is lower alkyl, cyclopropyl, and a phenyl group of the formula:

[phenyl-R₂]

wherein R₂ is one, two or three substituents independently selected from hydrogen, halogen, and $C_1$ to $C_4$ alkyl, halo substituted $C_1$ to $C_4$ alkyl, hydroxy substituted $C_1$ to $C_4$ alkyl, amino substituted $C_1$ to $C_4$ alkyl and R₁ is hydrogen or a carboxy-protecting group; and Z is selected from the group consisting of an aromatic heterocyclic ring having 5 or 6 atoms with one heteroatom selected from S, O and N and with the remaining atoms being carbon, and a phenyl group of the formula:

[phenyl-R₃]

wherein R₃ is one, two or three substituents independently selected from hydrogen, halogen, nitro, carboxyl, cyano, methoxy, $C_1$ to $C_4$ alkyl, halo substituted $C_1$ to $C_4$ alkyl, hydroxy substituted $C_1$ to $C_4$ alkyl, amino substituted $C_1$ to $C_4$ alkyl, loweralkylamino substituted $C_1$ to $C_4$ alkyl, haloloweralkylamino substituted $C_1$ to $C_4$ alkyl, hydroxyloweralkylamino substituted $C_1$ to $C_4$ alkyl, aminoloweralkylamino substituted $C_1$ to $C_4$ alkyl, a group having the formula Y—R₄ wherein Y is —O— or —S— and wherein R₄ is hydrogen or $C_1$ to $C_4$ alkyl, and an amine of the formula:

$$-N\begin{matrix}R_5\\|\\|\\R_6\end{matrix}$$

wherein
R₅ and R₆ are each independently hydrogen or $C_1$ to $C_4$ alkyl;
Z is also selected from substituted phenyl groups of the formulae A or B

[Structure A: phenyl with R₁ at quaternary carbon bearing (CH₂)ₙ and (CH₂)ₘ, with R₂ substituents]  (A)

[Structure B: phenyl with R₇ at quaternary carbon bearing (CH₂)ₙ, R₂ and (CH₂)ₘ, with R₂ substituent]  (B)

wherein n and m can be independently 0, 1, or 2 with R₇ being selected from S, O, N—R₈, or C₂ wherein R₈ is hydrogen, $C_1$ to $C_4$ alkyl, 1, $C_1$ to $C_4$ hydroxyalkyl, $C_1$ to $C_4$ haloalkyl, $C_1$ to $C_4$ aminoalkyl, $C_1$ to $C_4$ alkyl substituted aminoalkyl; and pharmaceutically acceptable salts thereof.

2. The compound of claim 1 wherein Z is pyrrole and R is p-fluorophenyl.

3. The compound of claim 1 wherein Z is pyridine and R is p-fluorophenyl.

4. The compound of claim 1 wherein Z is p-fluorophenyl and R is cyclopropyl.

5. The compound of claim 1 wherein Z is 2-furan and R is ethyl.

6. The compound of claim 1 wherein Z is p-methylphenyl and R is o,p-difluorophenyl.

* * * * *

UNITED STATES PATENT AND TRADEMARK OFFICE
CERTIFICATE OF CORRECTION

PATENT NO. : 4,762,845
DATED : August 9, 1988
INVENTOR(S) : Daniel Chu et al.

It is certified that error appears in the above-identified patent and that said Letters Patent is hereby corrected as shown below:

In Claim 1, Column 22, delete structure (A),

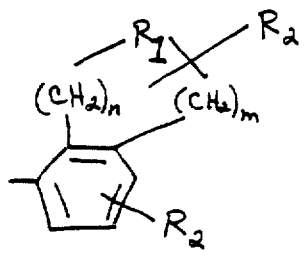

and substitute therefor, a new structure (A).

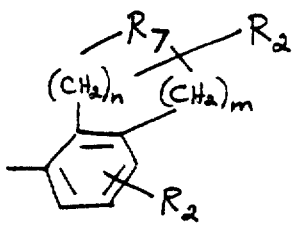

UNITED STATES PATENT AND TRADEMARK OFFICE
CERTIFICATE OF CORRECTION

PATENT NO. : 4,762,845

DATED : August 9, 1988

INVENTOR(S) : Daniel Chu et al.

It is certified that error appears in the above-identified patent and that said Letters Patent is hereby corrected as shown below:

In Claim 1, Column 22, Line 34, delete "$C_2$", and substitute therefor "$CH_2$".

In Claim 1, Column 22, Line 35, delete "1,", second instance.

Signed and Sealed this

Seventh Day of March, 1989

Attest:

DONALD J. QUIGG

*Attesting Officer*  *Commissioner of Patents and Trademarks*